United States Patent
Windeballe et al.

(10) Patent No.: US 11,931,287 B2
(45) Date of Patent: Mar. 19, 2024

(54) BODY SIDE MEMBER OF AN OSTOMY APPLIANCE

(71) Applicant: Coloplast A/S, Humlebaek (DK)

(72) Inventors: Lars Stendevad Windeballe, Virum (DK); Richard Morgan Hickmott, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 235 days.

(21) Appl. No.: 16/498,412

(22) PCT Filed: Apr. 9, 2018

(86) PCT No.: PCT/DK2018/050069
§ 371 (c)(1),
(2) Date: Sep. 27, 2019

(87) PCT Pub. No.: WO2018/188707
PCT Pub. Date: Oct. 18, 2018

(65) Prior Publication Data
US 2021/0113362 A1    Apr. 22, 2021

(30) Foreign Application Priority Data

Apr. 10, 2017    (DK) .......................... PA 2017 70256

(51) Int. Cl.
*A61F 5/443*    (2006.01)
*A61F 5/44*    (2006.01)

(52) U.S. Cl.
CPC ............. *A61F 5/443* (2013.01); *A61F 5/4404* (2013.01)

(58) Field of Classification Search
CPC ........ A61F 5/443; A61F 5/4404; A61F 13/00; A61F 13/15; A61F 5/445; A61F 5/44; A61L 24/00; A61L 24/0036; A61L 28/00; A61M 27/00; B65B 69/0016
See application file for complete search history.

(56) References Cited

U.S. PATENT DOCUMENTS

| | | | |
|---|---|---|---|
| 4,710,182 A | 12/1987 | Bryson | |
| 5,496,296 A * | 3/1996 | Holmberg | ............... A61F 5/443 604/336 |
| 5,769,831 A | 6/1998 | Freeman et al. | |
| 7,820,873 B2 * | 10/2010 | Sun | .......................... C08J 5/045 604/374 |
| 2006/0141016 A1 * | 6/2006 | Sambasivam | ........... A61P 17/00 424/773 |
| 2006/0200101 A1 | 9/2006 | Mullejans et al. | |

(Continued)

FOREIGN PATENT DOCUMENTS

| | | |
|---|---|---|
| CN | 1258208 A | 6/2000 |
| CN | 102413797 A | 4/2012 |

(Continued)

*Primary Examiner* — Adam Marcetich
*Assistant Examiner* — Rachel O'Connell
(74) *Attorney, Agent, or Firm* — Coloplast Corp., Coloplast A/S; Nick Baumann

(57) ABSTRACT

A body side member of an ostomy appliance comprising a cover layer forming a distal surface having one or more openings to allow egression of a releasable material to be shifted between a first position underneath the cover layer to a second position on top of the cover layer in use of the body side member around a stoma of a user.

25 Claims, 7 Drawing Sheets

(56) References Cited

U.S. PATENT DOCUMENTS

| | | | |
|---|---|---|---|
| 2008/0097361 A1* | 4/2008 | Fabo | A61F 5/443 604/338 |
| 2010/0022933 A1 | 1/2010 | Oelund et al. | |
| 2010/0145291 A1* | 6/2010 | Kambara | A61F 13/8405 604/333 |
| 2010/0324511 A1 | 12/2010 | Dove et al. | |
| 2011/0040270 A1 | 2/2011 | Ciok et al. | |
| 2011/0213322 A1* | 9/2011 | Cramer | A61F 5/443 604/344 |
| 2012/0010636 A1* | 1/2012 | Boey | A61L 31/10 606/151 |
| 2012/0041404 A1 | 2/2012 | Bach et al. | |
| 2012/0302981 A1* | 11/2012 | Lam | A61F 5/445 604/344 |
| 2013/0123678 A1* | 5/2013 | Carty | A61F 13/0253 602/54 |
| 2013/0274696 A1 | 10/2013 | Lam | |
| 2013/0304008 A1 | 11/2013 | Hanuka et al. | |
| 2014/0128825 A1 | 5/2014 | Klein et al. | |
| 2015/0297389 A1 | 10/2015 | Nyberg | |
| 2020/0015996 A1* | 1/2020 | Schertiger | A61F 5/4401 |
| 2021/0275341 A1* | 9/2021 | Hansen | A61L 15/60 |

FOREIGN PATENT DOCUMENTS

| | | | | |
|---|---|---|---|---|
| CN | 104837442 A | 8/2015 | | |
| CN | 105407841 A | 3/2016 | | |
| EP | 0686381 A1 | 12/1995 | | |
| RU | 2525209 C2 | 8/2014 | | |
| RU | 2553934 C2 | 6/2015 | | |
| RU | 2598804 C2 | 9/2016 | | |
| RU | 2602034 C2 | 11/2016 | | |
| WO | 2010060116 A1 | 5/2010 | | |
| WO | WO-2014028357 A1 * | 2/2014 | | A61F 2/0063 |

* cited by examiner

BODY SIDE MEMBER OF AN OSTOMY APPLIANCE

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and for these ostomists in particular safe, reliable and efficient ostomy devices are highly desirable. Numerous attempts have been made to provide ostomy devices to meet such requirements, e.g. the requirement of prolonged wear time, but the provision of sufficient efficiency to achieve a satisfactory long wear time of ostomy devices continues to be an unmet need.

Ostomists and health care professionals alike would welcome improvements in ostomy devices to better meet such requirements.

SUMMARY

The present disclosure provides aspects of a body side member of an ostomy appliance according to the appended claims. The disclosure further provides an ostomy appliance including a body side member as disclosed herein.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5 is a schematic cross-sectional view of one embodiment of a cover layer of a body side member comprising an opening allowing the releasable material to egress through.

DETAILED DESCRIPTION

Figure 1:
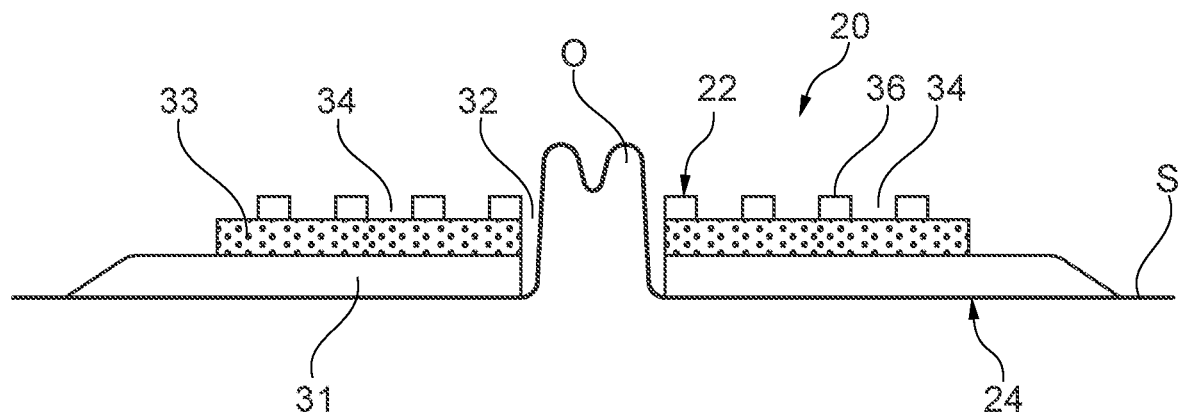
FIG. 1 is a schematic, cross-sectional view of one embodiment of a body side member of an ostomy appliance comprising a releasable material.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading," "trailing," etc., is used with reference to the orientation of the Figure(s) being described. Because components of embodiments can be positioned in different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output", "waste(s)", and "fluids" interchangeably. A subject having undergone ostomy surgery may be referred to as "ostomist" or "ostomate" moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

Moreover, "releasable material" should be interpreted to include moldable and squeezable materials as well as including permanently deformable and shape-memory materials (i.e. materials capable of recovering to their original shape after a deformation). Also, in some implementations, the releasable material may be non-deformable itself (i.e. no significant deformation of the dimensions of a mass or volume "per volume unit" of the material is possible). However, it is possible to manipulate the material in the sense of moving it in relation to other components. Additionally, or alternatively, "releasable" should be interpreted to relate to any materials that can be moved and/or manipulated by the hands or fingers of an average person without using significant force. In embodiments, the releasable material is a sacrificial component of the body side member, i.e. a material suitable for being "sacrificed" to avoid or slow the breaking down of the adhesive of the body side member and/or any of the other components of the body side member.

The use of the phrase "substantially" as a qualifier of certain features or effects in this disclosure, is intended to simply mean that any deviations are within tolerances that would normally be expected by the skilled person in the relevant field.

In one aspect, the present disclosure relates to a body side member of an ostomy appliance comprising a proximal surface and a distal surface. At least a portion of the proximal surface comprises an adhesive. The body side member comprises a centre portion. At least the centre portion is prepared for the provision of a stoma receiving opening extending through the body side member. The body side member includes a cover layer forming at least a portion of the distal surface. The body side member further includes a releasable material provided proximal to the cover layer. The cover layer of the body side member is configured to comprise one or more openings, each being configured to allow egression of the releasable material onto the distal surface of the body side member (by the releasable material passing through one or more openings in the cover layer), at least in use of the body side member around a stoma of a user. "At least in use" should be interpreted such that, as long as the body side member is not prepared for, or attached to, the skin surface of a user, the releasable material is not intended to egress (release through the cover layer) onto the distal surface of the body side member.

The proximal surface of the body side member comprises an adhesive. In embodiments, the adhesive comprises a plurality of different adhesive materials. In one embodiment, the different adhesive materials of the adhesive are provided in a side-by-side manner. In one embodiment, the different adhesive materials of the adhesive are provided as a layered structure. In one embodiment, the different adhesive materials of the adhesive are provided primarily side-by-side, but with some overlapping portions of the different adhesive materials. Examples of suitable adhesive materials are given below.

The releasable material is provided inter alia to provide a better sealing effect between the body side member and that part of the surface of the skin of a user that surrounds the stoma. When the seal or sealing effect is improved, the likelihood of stomal fluids bypassing that seal and cumulating underneath the body side member, i.e. between the user's skin surface and the device, is reduced. Thereby stomal fluids, which often contain very aggressive bodily substances (e.g. including certain enzymes produced in the body), are prevented from reaching the polymeric matrix of the adhesive on the proximal surface of the device. This in turn helps to avoid both damage to the skin surface (caused by the aggressive stomal fluids), and disintegration and/or failure of the adhesive. This further provides a body side member having improved security against leakage and longer wear time (i.e. the time between substitutions of a used product for a fresh one). A longer product wear time may itself help provide less skin complications, since removal of the adhesive body side member of some appliances currently available from the skin surface tends to strip the skin cells of the epidermis. Thus, by achieving a longer wear time of the product, less product substitutions are required, resulting in fewer occurrences of potential skin cell stripping. Additionally, there is an economic benefit to the user and/or to the health care system/insurance provider, when less substitutions and thus less products are needed.

One way in which the body side member of the present disclosure allows for an improved sealing effect, is by allowing the releasable material to egress through the one or more openings in the cover layer and into contact with stomal output. Thereby, the improved sealing effect is at least partly provided by an increase in the amount of material the aggressive stomal fluids must break down to reach the adhesive on the body side member. As such, the releasable material is provided as a sacrificial component of the body side member, i.e. a material that is suitable for being "sacrificed" to avoid or slow the breaking down of the adhesive of the body side member.

The cover layer forms at least a portion of the distal surface of the body side member and is configured to comprise one or more openings. In embodiments, the cover layer is configured to provide or define an entirety of the distal surface of the body side member, including the centre portion. In other embodiments, the cover layer can be configured to extend over and cover only a portion of the distal surface, i.e. configured such that it only extends over a portion of a radial distance between the centre portion and/or the stoma receiving opening and an outermost edge or outermost edge portion of the body side member.

Regarding the one or more openings, the cover layer can be provided with the one or more openings during manufacture such that, when the user receives the body side member product, each of the one or more openings is/are present in the cover layer. However, it is also envisioned that one or more openings can be provided by the user (or the HCP) in the cover layer immediately before application of the body side member to the skin surface of the user. Also, one or more openings beings provided at manufacture may be supplemented by one or more further openings provided by the user before application. These options allow for additional individual customization of the body side member. As an example, the user may be able to control both the amount and optimal location(s) of the one or more openings on the body side member, i.e. the user has the option to allow more releasable material to egress at certain locations of the distal surface of the body side member where the material is mostly needed.

Each of the one or more openings are configured to allow egression of the releasable material onto the distal surface of the body side member, when the body side member is being used. "Egression" should be interpreted as "the act of coming out" or "becoming apparent." Thus, "egression" is intended to mean that the releasable material can come out of the one or more openings, or become apparent, i.e. become present, visible and/or available on the distal surface of the body side member. Moreover, "egression" of the releasable material is intended to cover situations wherein the releasable material is deliberately or consciously manipulated (such as by finger pressure of the user) out of one or more openings, and situations wherein the releasable material exits or passes through an opening ("egress") without any force or interaction provided by the user. In embodiments, the latter kind of situations may be a result of expansion of the releasable material, e.g. occasioned by uptake of moisture from the mucous membrane of the stoma, moisture from the skin surface of the user, moisture in the stomal output and/or a combination of these factors.

The cover layer is configured to include the one or more openings and allow the egression of releasable material onto the distal surface of the body side member. As such, the one or more openings can be considered provided in the distal surface of the body side member, or at least in a portion of the distal surface formed by the cover layer. In embodiments, wherein the cover layer only forms a portion of the distal surface of the body side member, the one or more openings can be considered as comprised by the cover layer in the one or more portions of the distal surface not covered by the cover layer. In embodiments, an outermost edge portion of the distal surface is not covered by the cover layer (radial dimension of cover layer less than radial dimension of body side member in that portion); thus, one opening in the cover layer is formed at that outermost edge portion. In one embodiment, the cover layer includes one opening at an outermost edge of the cover layer and configured by at least a portion of the cover layer, having a first radial extent dimension, being smaller than a second, average radial extent dimension, of the body side member. In particular, but not exclusively, this is advantageous if the configuration of the body side member must be customized to egress the releasable material at an outermost edge portion of the body side member. Examples of the need for such a configuration are in cases of loop- or temporary stomas, or if the body side member is applied near two or more stomas or fistulas. Skin surface areas suffering from one or more fistulas in themselves, or in combination with one or more stomas, can be extremely difficult to "treat" or cover efficiently and without causing pain to the user/patient with standard type ostomy appliances. Thus, the present disclosure provides options for expanding the HCP's options for providing the necessary care in these instances. By analogy, the one opening may also or instead be provided at an innermost edge portion (for example, but not limited to, in the centre portion) adjacent and/or around the stoma receiving opening.

In embodiments, the cover layer includes one or more radial protrusions extending radially away from an outermost edge of the cover layer. In embodiments, the cover layer includes one or more radial protrusions extending radially away from an outermost edge of the body side member. In one embodiment, the one or more radially extending protrusions form attachment means for attaching the cover layer to the body side member. In one embodiment, the one or more radially extending protrusions are configured to form hinges facilitating easy attachment and/or handling of the cover layer to the body side member.

The one or more openings are configured to allow egression of the releasable material onto the distal surface of the body side member. Releasable material egressing out of the one or more openings functions as a sacrificial material component of the body side member, i.e. a material that is suitable for being "sacrificed" to avoid or slow the breaking down of the adhesive on the proximal surface of the body side member. This is advantageous in that the damaging effects of the aggressive stomal fluids on the primary adhesive, carrying the weight and creating the seal to the user's skin, of the ostomy appliance, are attenuated by sacrificing the releasable material. This in turn helps mitigating or at least prolonging the time needed for such stomal fluids to break down the adhesive on the proximal surface of the body side member. Thereby, an advantageous extension of the wear time of the ostomy appliance is achieved. Studies conducted by the inventors show that ensuring an unobstructed and efficient release of sacrificial material to engage with the aggressive stomal output provide promising results in terms of significantly reducing the rate or speed of breakdown of the adhesive, and thus allows for increased wear time (life time) of the body side member. Moreover, the studies further suggest that for some implementations of the invention of the present disclosure, such efficient and unobstructed release is a factor having more weight than specifically controlling the direction of the releasable material to be sacrificed towards the stoma surface and/or an area of the body side member adjacent to the stoma and/or the stoma receiving opening.

In addition, experience shows that when an innermost edge portion of the body side member, or the centre portion of the body side member immediately adjacent to, or surrounding the stoma receiving opening, is engaged ("attacked") by aggressive stomal fluids, it may often cause a surprisingly (fast) break-down of the adhesive of the proximal surface of the body side member starting from that innermost edge portion and egressing radially therefrom. This may in turn lead to failure of the adhesive, thus rendering the body side member and/or the whole ostomy appliance useless. Prior solutions focused on addressing such problems at the area of a body side member immediately adjacent to the stoma; i.e., the prior solutions tried to solve the issues at the innermost edge portion of the body side member.

Contrary to this, the present disclosure provides different and inventive solutions to overcome these and other problems, because at least in some approaches, the problems are believed to be mitigated or reduced wholly or partly, because of the better options for distributing how and where the releasable material egress out of the one or more openings. By way of example, but not exclusively, this is achieved by distributing or "spreading" the releasable material over a larger or even all the distal surface of the body side member. In this regard, the inventors have found that, if the body side member is configured such that the releasable material enters onto the distal surface of the body side member, instead of being primarily directed towards the stoma's surface (the mucous membrane), and/or towards an area or location of the body side member immediately adjacent the stoma, the beneficial effects of the releasable material may be reached to the same or even to a better extent than by only directing the releasable material towards the stoma. In other words, providing the one or more openings in the cover layer allows for a release (egression) of the releasable material predominantly in a distal direction of the body side member, instead of only releasing material in a radial direction towards the stoma.

In embodiments, the releasable material egress out of the one or more openings by providing finger pressure to the distal surface of the body side member adjacent respective one or more openings. If more sacrificial material is needed in one or more locations, in particular vulnerable locations where the body side member is known to be prone to leakage, the user can make more releasable material egress out in such localized areas by particularly focusing on the one or more openings of that specific area. In embodiments, the releasable material is adapted to egress through each of the one or more openings in response to finger pressure being applied to a portion of the distal surface of the body side member adjacent a respective opening. Additionally, or alternatively, the user does not provide pressure on the distal surface adjacent the one or more openings, and instead the releasable material may egress out of the one or more openings when the level of breakdown of the adhesive of the body side member reaches the one or more openings, position(s) of the one or more openings then configured to correspond to a certain lower threshold value for acceptable adhesive breakdown levels. This may help provide additional control of when and how much releasable material can and will be released. Moreover, these embodiments may help provide a simpler construction and still achieve the beneficial effects on sealing between the body side member and the skin and thus the increased wear time.

In embodiments, the improved sealing effect of the body side member can be achieved after applying the body side member to the user's skin surface (adhering the adhesive proximal side to the skin) by providing finger pressure to an area around the one or more openings on the distal surface, to effectively manipulate and thereby move the releasable material out onto the distal surface of the body side member. In embodiments, the releasable material can thereby be shifted between at least a first and a second position in relation to the cover layer. In embodiments, the cover layer is configured to be plastically or elastically deformable, such as, but not limited to, by forming the cover layer from an anisotropic material.

In one embodiment, the releasable material is provided below or underneath the one or more openings in the first position, and at least some of the releasable material is provided outside the one or more openings in the second position. Also, in the second position, a first portion or some of the releasable material may be located underneath an opening and a second portion or some of the releasable material may be located outside (has egressed out of) the opening. In embodiments, some or all of the releasable material is located underneath the cover layer in the first position, and some or all of the releasable material is located above or "on top" of the cover layer in the second position.

In one embodiment, the releasable material is configured to swell in response to absorption of moisture. In embodiments, the releasable material is configured to undergo a swelling action by absorption of moisture from the stomal output and/or from mucus emanating from the mucous membrane of the stoma. In embodiments, the swelling of the releasable material helps create an improved seal between the stoma and the body side member, thereby reducing the probability of leakage caused by stomal fluids attacking the adhesive on the proximal surface of the body side member. In embodiments, the releasable material includes a moisture absorbing component or substance. In embodiments, the moisture absorbing component has a high absorption capability or potential and in other embodiments, the moisture absorbing component has a small absorption capability. Suitable materials for the moisture absorbing component include, but are not limited to, superabsorbent polymers commonly made from poly-acrylic acid salts. In further embodiments, the adhesive of the proximal surface of the body side member is configured to undergo a swelling action by absorption of moisture and thus help create an improved seal between the stoma and the body side member. In embodiments, both the adhesive of the proximal surface of the body side member and releasable material are configured to undergo a swelling action by absorption of moisture. In one embodiment, the releasable material is a viscoelastic material.

In one embodiment, the body side member further comprises a reinforcing element. The reinforcing element may particularly, but not exclusively, include a sheet or layer of a polymeric film material, such as polyethylene (PE) or polypropylene (PP). Other film materials having additional characteristics, e.g. higher/lower liquid-, vapor- or gas-impermeability or odour control and others, may additionally and/or alternatively be used. Other reinforcing element options include mesh or mesh-shaped and/or woven materials. In one embodiment, the reinforcing element can be located between the adhesive on the proximal surface and the cover layer. In one embodiment, the reinforcing element can be embedded (contained completely) in the adhesive of the proximal surface of the body side member. In one embodiment, the reinforcing element includes reinforcing fibres.

One advantageous effect of the reinforcing element is that it helps provide a body side member which is more resistant to forces acting on it. Often a stoma is located on the lower portion of the abdomen of the user (corresponding to the location of the intestines). Thus, some examples of forces acting on the body side member include forces generated by the clothes of the user, such as at the waist lining of a pair of pants or jeans, such forces often further amplified by the presence of a belt. The forces may be both pressure and shear forces, often in combination.

In one embodiment, the cover layer of the body side member comprises a sheet material. The sheet material may particularly, but not exclusively, include a sheet or layer of a polymeric film material, such as PE or PP. Other film materials having additional characteristics, e.g. higher/lower liquid-, vapor- or gas-impermeability or odour control and others, may additionally and/or alternatively be used. In one embodiment, the sheet material layer is dissolvable.

In one embodiment, the cover layer is formed as a separate component and is configured to be attachable to other components of the body side member. As such, the cover layer may be a "loose" component which is provided together with the body side member, but which is not initially attached to the body side member (i.e. not attached during the manufacturing process). In embodiments, the cover layer is formed as a separate component and is configured to be attachable to other components of the body side member and to be attached distal to the releasable material.

In embodiments, the cover layer is only locally fastened, i.e. the cover layer is only attached to the body side member in a certain number of individual locations, each forming only a small portion of the body side member. In one embodiment, the cover layer is attached to the body side member by hinges or hinge means, including living hinges. In such embodiments, the cover layer may be movably attached to the body side member in some locations while not being attached to the body side member in other locations.

In one embodiment, the cover layer is formed as an integral component of the structure of the body side member. This means that the cover layer is connected to or attached to the body side member during the manufacturing process. In such embodiments, it is thus not a separate component to be subsequently connected to the body side member. The cover layer can be connected or attached over an entirety of the portion of the distal surface covered by the cover layer facing the distal surface of the body side member. Alternatively, it can be connected or attached in two or more localized places or points. The attachment or connection to the other components of the body side member may be provided by welding, such as heat welding or ultrasound welding, or by adhesion of the components to each other. Adhesion may in such case be provided by the adhesive effect of a distal surface of the adhesive of the body side member or by additional adhesive material being disposed on either the distal surface of the body side member, or on the surface of the cover layer facing the distal surface of the body side member. In one embodiment, also at least a portion of a distal surface of the body side member comprises an adhesive. In one embodiment, an adhesive of the proximal surface of the body side member and an adhesive of the distal surface of the body side member are identical adhesives. In one embodiment, one coherent adhesive material forms both the proximal surface and the distal surface of the body side member. Other means or ways of attaching or connecting the components of the body side member to each other may be applied.

In one embodiment, the cover layer is dissolvable when subjected to water or a watery liquid, such as aggressive stomal fluids or mucus emanating or secreting from the mucous membrane of the stoma. In one embodiment, the dissolvable cover layer comprises one or more polyvinyl alcohol polymers.

In one embodiment, the cover layer comprises a thermoformable material. In one embodiment, the cover layer is formed of a thermoplastic polymer. In one embodiments, the cover layer comprises an elastic material.

In one embodiment, the cover layer is additionally capable of transmitting moisture and may e.g. be made from polymers such as polyolefin types e.g. PE, PP or polybutylene, polyurethane, polyvinyl alcohol, ethylene vinyl acetate or other thermoplastic polysaccharides, polyether block amides such as PEBAX® from Arkema, France, block copolymers like styrene-isoprene-styrene block copolymers or ethylene acrylate block copolymers, polyesters such as polyethylene terephthalate (PET) or derivates thereof and any laminates made from such polymers. In embodiments, the cover layer comprises a thin foam layer made from e.g. polyurethane, polyethylene or polyvinyl acetate.

In embodiments, the cover layer comprises a differentiated thickness when viewed over a total extent of the cover layer. In one embodiment, a thickness of the cover layer decreases from a greater thickness at an outermost edge portion of the cover layer to be thinner radially closer to the centre portion of the body side member. The differentiated thickness of the cover layer is believed to be useful in providing a smooth egression of the releasable material from the one or more openings.

In embodiments, the cover layer is formed by a resilient material. In some implementations, such a resilient material facilitates egression of the releasable material from the one or more openings, particularly because the resiliency of the material causes the portion of the cover layer adjacent to an opening to return to its original/initial shape after the cover layer around the opening has been manipulated by finger pressure. Suitable resilient materials for the cover layer include, but are not limited to, thermoplastic elastomers (TPE's) and/or mixtures thereof. In embodiments, cover layer is made by injection molding. Alternatively, or additionally, the cover layer is made in a two-component casting process, advantageously in combination with the provision of a first half of a coupling interface of the ostomy appliance.

In embodiments, the one or more openings comprise one or more circular perforations in the cover layer. In embodiments, the one or more circular perforations allow for a relatively uniform egression of the releasable material through the cover layer and onto the distal surface of the body side member. Moreover, this provides particularly advantageous embodiments for the body side member to be configured for "automatic" egression of releasable material, i.e. for embodiments in which the user does not have to provide pressure on the cover layer or otherwise interact with the body side member to make the releasable material egress through the one or more openings in the cover layer.

In embodiments, the cover layer comprises a plurality (i.e. more than two) of circular perforations each having a widest diameter in a range of 2-10 mm. This range of widest diameter provides openings exhibiting a good balance between ease of egression of the releasable material through the openings, and the user's choice and chance of controlling the rate of release of the releasable material. In embodiments, a preferred widest diameter of an opening may be in the higher end of the range for releasable materials of low viscosity (more solid-like), and in the lower end of the range for releasable materials of high viscosity (more fluid-like). In some implementations, the deciding factor for choice of widest diameter of the one or more openings is chosen based on how much moisture should be allowed to come into contact with the releasable material through an opening. In further embodiments, the cover layer comprises different sized (different diameters of) openings.

In embodiments, the plurality of openings is localized in one or more zones of the distal surface of the body side member. This provides another option for the user to control in which particular locations more releasable material can be egressed out of the openings, and in which locations less releasable material can be egressed.

In embodiments, the one or more openings comprise(s) one or more slitted perforations in the cover layer. In embodiments, a slitted perforation is provided in a straight line extending between two points of the cover layer. In one embodiment, each slitted perforation fully penetrates the cover layer. In another embodiment, each slitted perforation only partially penetrates the cover layer. In embodiments, each slitted perforation is provided in a straight line extending in the radial direction of the cover layer. In embodiments, the straight line of each slitted perforation extends from a point located radially outward of the centre portion of the body side member to a point located approximately ⅕-¼ of the radial distance between an innermost edge portion of the body side member around the stoma receiving opening and an outermost edge of the body side member. In other embodiments, each slitted perforation is provided in a curved line.

In one embodiment, the cover layer comprises one slitted perforation provided in a spiral shape in the cover layer. The spiral shape of the one perforation provides another option for the user to customize the body side member in terms of how much releasable material he or she wants to initially egress through the spiral shaped opening. Whereas the radially slitted perforations provide options for egressing releasable material in one or more arcuate segments of the body side member, the spiral shaped perforations provide options for egressing material gradually, either starting from a radially outermost edge portion of the body side member or from a radially innermost edge portion of the body side member.

In embodiments, each of the one or more openings comprises a hinged gate formed in the cover layer. In embodiments, the hinged gate is provided by making a c-shaped or a u-shaped perforation in the cover layer, such that a minor portion of each gate "hinges" onto the cover layer. In other words, each hinged gate takes the form of a flap of the cover layer. Releasable material egressing out of, or from, the one or more openings comprising a hinged gate or flap acts to push the flap open or aside, and thereby allow sacrificial material to enter onto the distal surface of the body side member. Moreover, the hinged gate or flap additionally serves to protect the underlying layers and/or material by slowing or even preventing ingression of moisture or stomal output through the openings. In embodiments, this feature further provides additional options for differentiating egression of releasable material and/or ingression of moisture of the body side member. This provides for further controlling the distribution of releasable material on the distal surface of the body side member, i.e. controlling where and how and how much releasable material to be sacrificed is egressed from the one or more openings.

In embodiments, the releasable material is a fluid or a liquid. In embodiments, the releasable material is a pasta or paste. In embodiments, the releasable material is a gel or a substance or material suitable for gelling when exposed to certain conditions, such as exposed to moisture. In embodiments, the plurality of different materials of the releasable material is provided as a composition. In embodiments, the plurality of different materials of the releasable material is provided as a compound. In embodiments, the composition or compound comprises two or more substances.

In embodiments, the releasable material comprises a matrix. In embodiments, the matrix of releasable material further comprises a neutralizing substance incorporated therein. In embodiments, the matrix of releasable material is in the form of a gel, a foam, a film layer, paper or a coating, such as a solid coating or a powder coating. In embodiments, the matrix of releasable material and the neutralizing substance combine to form a colloidal solution, such as a sol. In embodiments, the releasable material or the matrix of the releasable material comprises one or more medicaments. In embodiments, the one or more medicaments is/are suitable for alleviating pain and/or problematic skin surface conditions of the peristomal skin surface.

In embodiments, the body side member is configured to allow respective, individual materials of the plurality of different materials of the releasable material to egress onto the distal surface of the body side member through two or more individual and different openings. Thereby, the body side member can be configured such that one opening or a first group of openings is configured to egress one type of releasable material, and another opening or second group of openings is configured to egress a different type of releasable material. Alternatively, or additionally, in embodiments, the size and configuration of the individual openings can be differentiated. By providing differentiated openings in combination with allowing different releasable materials egress from different openings, the beneficial effects of improved sealing capability of the body side member can be achieved in a differentiated degree or manner across a plurality of configuration combinations, thus providing a versatile product providing the user with many options for customizing the body side member according to individual requirements. In embodiments, more than two different types of releasable materials and/or more than two openings, or more than two groups of openings, can be configured accordingly.

In embodiments, the releasable material is provided in a layer. This provides a body side member of relatively simple structure, which is advantageous for mass production. In embodiments, the layer of releasable material is provided between the adhesive of the proximal surface of the body side member and the cover layer forming at least a portion of the distal surface of the body side member. In embodiments, the layer of releasable material is formed as two or more concentric and annular zones or rings each separated from another by a zone in which no releasable material is present. In embodiments, each concentric ring containing releasable material is configured to coincide, in an axial direction of the body side member, with one opening or a group of openings being at a predetermined radial distance from the stoma receiving opening. In embodiments, each of the concentric rings is configured with different releasable materials, or with different amounts of releasable material, such as, but not limited to providing each ring with different (layer) thicknesses.

In embodiments, the cover layer forms the distal surface of the body side member. In embodiments, the sheet material comprised by the cover layer forms the distal surface of the body side member. In embodiments, a proximal surface of the cover layer, or of the sheet material of the cover layer, comprises an adhesive providing the adhesive of the proximal surface of the body side member.

In embodiments, the body side member includes a cover layer formed of erodible material and further includes a relatively thin protective layer or coating provided on the distal surface of the erodible cover layer provided to prevent or slow erosion or break-down thereof by aggressive stomal output gathering at the distal surface of the body side member. The protective layer or coating includes a "one-way" (unidirectionally permeable) material allowing moisture to penetrate through the protective layer or coating into the erodible cover layer. In such embodiments, the erosion rate of the erodible cover layer can be controlled, e.g. by controlling the permeability parameters of the protective layer. Thereby, the body side member can be configured such that an entirety of the cover layer is dislodged when a certain predeterminable amount of moisture has penetrated the protective layer. This is advantageous for achieving a body side member wherein the release of, or the engagement between, the stomal output and the releasable material of the body side member, can be delayed or postponed, and/or for controlling where the exposure of the adhesive of the proximal surface of the body side member to the stomal output occurs.

Pressure sensitive adhesives, particularly those containing hydrocolloids, is a particularly suitable group of adhesives being characterized by having a particulate phase of hydrocolloids dispersed in the adhesive phase or matrix. Adhesive containing hydrocolloids may absorb moisture from the skin to avoid occlusion of the skin, while maintaining its adhesive properties to skin. Moreover, an adhesive body containing hydrocolloids may have any thickness and still have the non-occlusive properties. A hydrocolloid adhesive may be processed as a hot melt and is easily moulded into specific shapes.

A typical pressure sensitive adhesive composition comprises a substantially homogeneous mixture of 10-60 weight percent of one or more rubbery elastomeric components, 5-60% of one or more absorbent particles, 0-50% tackifier resin, 0-10% of a plasticiser and 0-60% of a non-polar oily extender, based on the total weight of the composition. The rubbery elastomeric base could be selected from the group consisting of physically cross-linked elastomers (suitably block copolymers containing polystyrene blocks), a chemically cross-linked natural or synthetic rubbery elastomer, or a rubbery homopolymer. A physically cross-linked elastomer selected from block-copolymers of styrene, and one or more butadienes may be a styrene-butadiene-styrene block copolymer, a styrene-isoprene copolymer and is preferably a mixture of styrene-isoprene-styrene and styrene-isoprene block copolymers. A chemically cross-linked rubbery elastomer may be e.g. butyl rubber or natural rubber. A rubbery homopolymer may be a polymer of a lower alkene such as low density polyethylene or propylene, preferably atactic polypropylene or polyisobutylene. A tackifying resin optionally used in accordance with the invention is preferably a hydrogenated tackifier resin and is more preferred selected from a group comprising polymers and copolymers of cyclopentadiene, dicyclopentadiene, alpha-pinene or beta-pinene. When the physically cross-linked elastomer is a styrene-butadiene-styrene block copolymer or a styrene-isoprene-styrene block copolymer, the adhesive suitably comprises 0-10% of a plasticiser (e.g. CITROFOL® BIL Jungbunzlauer, Switzerland). The hydrocolloid particles preferably consist of one or more water-soluble or water swelling hydrocolloid polymers or gums. In other embodiments, the adhesive of the proximal surface of the body side member comprises one or more adhesives of the types disclosed in publications WO2007/082538 and WO2009/006901.

In embodiments, each of the one or more openings provides a passage between an underside and a top side of the cover layer. Each opening provides a passage for releasable material to exit or egress through, and/or for liquid or moisture, such as generated by stomal output, to enter through into the opening and to the underside of the cover layer. At least in the latter case, a capillary action between the entering moisture and the releasable material can result in the releasable material egressing out of the opening.

The releasable material can be configured to swell in response to absorption of moisture which can also cause the releasable material to externalize and be dispensed through the openings. Depending, among other factors, on the nature of the releasable material, in some embodiments moisture absorption and a resulting swelling of the releasable material initiates the egression of the releasable material without any manipulation of the cover layer adjacent to the one or more openings being required by the user. In other words, the egression of the releasable material through the one or more openings may start "automatically" as soon the releasable material begins to take up moisture. It has been found that the rate of the egression of the releasable material can be surprisingly high, thereby causing a fast release of the releasable material through the one or more openings onto the distal surface of the body side member. This may also be helpful in guiding the releasable material quickly towards the stoma, where it is "sacrificed" to the stomal output, thereby providing faster and thus better security against leakage caused by the aggressive stomal output. This is further advantageous because no active participation by the user is required for the egression of the releasable material through the one or more openings.

In embodiments, one or more openings of the cover layer is/are located radially closest to the centre portion of the body side member. In another embodiment, each of the one or more openings are located at a radially outermost portion of the body side member. This is particularly suitable for helping to provide a distribution of the releasable material over a larger portion, or even an entirety of the distal surface of the body side member in use.

In embodiments, the one or more openings of the cover layer can be distributed in a pattern over the surface of the cover layer. The pattern may be a symmetrical or a random pattern.

In embodiments, the adhesive of the proximal surface of the body side member is provided on a backing layer, the backing layer being distal to the adhesive of the proximal surface and proximal to the releasable material. In embodiments, the backing layer includes a film. In embodiments, the film includes a polyolefin material. In embodiments, the film material includes polyethylene. In embodiments, the backing layer carries the adhesive of the proximal surface of the body side member. In embodiments, the releasable material is provided on a distal surface of the backing layer. In embodiments, the releasable material includes a layer being located on the distal surface of the backing layer. In embodiments, the releasable material layer is attached to the distal surface of the backing film by one or more welds or welding zones, or by adhesion. In embodiments, the cover layer is provided distal to the releasable material layer. Thus, these embodiments provide an advantageous simple construction of the body side member, which can be processed in a fast and reliable production process keeping manufacturing costs low while providing a new and versatile body side member for an ostomy appliance with several options for creating a customized and improved sealing to the skin surface.

In embodiments, the releasable material is configured to be dispensed through the one or more openings. Thereby, the releasable material can egress out of the one or more openings to enter onto a substantial portion of the distal surface of the body side member. In addition, the one or more openings can be configured such that this egression happens relatively quickly, such as in little time to provide a large surface area of sacrificial material to mitigate the damaging effects of the stomal output. In embodiments, the one or more openings may additionally be configured to open towards different directions. This allows for a versatile distribution of the releasable material, and in turn provides an option for an even distribution of releasable material over the entire distal surface of the body side member. Moreover, this provides a body side member offering many uses while having a relatively simple structure. Additionally, or alternatively, a cover layer having a plurality of openings may provide an option for differentiating the amount of releasable material at any locality on the distal surface of the body side member. This is particularly advantageous in that more releasable material may be guided or directed to a location where it may be more needed than elsewhere on the distal surface of the body side member. Particularly, the releasable material can be guided both towards the stoma and away from it. Such implementations allow for multiple options for addressing the releasable material's beneficial effects to the right locations, where a leakage problem may be occurring or where the user's experience tells him/her that leakage often occurs. In embodiments, the cover layer includes a plurality of openings. One or more of the plurality of openings can be configured to face axially away from the distal surface of the body side member, and thus help to direct releasable material to one or more locations where it is available for an extended period compared to when it is immediately subjected to stomal output.

In embodiments, the releasable material is configured to be dispensed through the one or more openings. By 'dispensed' is to be understood that in some implementations, for the releasable material to egress through or out of an opening, the cover layer adjacent to and surrounding the opening is to be manipulated by a user's fingers. In other words, 'dispensed' should be interpreted to mean that the egression of releasable material constitutes an action or step that requires active participation or contribution by the user. In embodiments, a distal surface of the cover layer includes texture for facilitating easier tactile recognition of where to manipulate the cover layer to make releasable material egress out of the opening. The texture is further useful in preventing the user's fingers from slipping off the surface of the cover layer during such manipulation.

In one exemplary implementation and application of the body side member according to the present disclosure, a user initially customizes, such as by cutting, a stoma-receiving opening to an approximate size or circumference of the user's individual stoma. Next, the user can remove any protective liner(s) provided on the body side member, such as on the adhesive of the proximal surface of the body side member and apply the body side member to the skin surface around the stoma. The user can then apply finger pressure to portions of the cover layer around each of the one or more openings to egress the releasable material out of the one or more openings.

From the above, it is understood that in conceiving the invention of the present disclosure, the inventors realized that the releasable material does not per se have to be provided close to, or in direct contact with the stoma's surface, or on the peristomal skin surface, for the releasable material to provide its beneficial effect on the sealing between the skin surface and the body side member. Indeed, it was realized that the effect is achievable to a significant extent by releasing releasable material on the distal surface of the body side member, i.e. on the surface of the body side member facing away from the skin of the user, when the body side member is used. This is believed to be at least partly because of the provision of the releasable material as a sacrificial material and/or the creation of additional surface area of this sacrificial material by distributing it over a larger area of the body side member.

Other helpful effects are envisioned by the body side member according to the disclosure, some of which effects are believed to be at least partly controllable by the applied number of openings and by the composition of the releasable material. In embodiments, more than one kind of releasable material can be provided underneath the cover layer, thereby allowing for different releasable materials to be released through different openings. Thereby, it is believed that more than one helpful effect can be achieved by the claimed body side member. Even further, as an example, in embodiments wherein more than one kind of releasable material is provided in one or more openings of the body side member, the helpful effect(s) presented by one releasable material may be amplified by the presence of another kind of releasable material to provide even better results in terms of reduction or elimination of leakage incidents.

In embodiments, the distal surface of the body side member comprises a first half of a coupling interface for coupling the body side member to a stomal output collecting bag. In one embodiment, the coupling half is a flange adapted to provide a surface for attaching another coupling half in the form of an adhesive flange provided on a stomal output collecting bag. In embodiments, the first half of the coupling interface is configured as a flexible, planar annular flange optionally comprising an adhesive. The first coupling half is adapted to couple with a second coupling half provided around an inlet opening of a stomal output collecting bag by means of an adhesive. The adhesive coupling may provide a releasable or a permanent adhesive coupling engagement between the components.

In embodiments, the coupling half is an annular ring comprising an upstanding flange protruding from the distal surface perpendicular thereto for attaching another coupling half in the form of a coupling ring provided on a stomal output collecting bag. In one embodiment, a first coupling half is attached to the distal surface of the body side member. In embodiments, the first coupling half is attached to the distal surface by an adhesive or by welding, but other ways of attaching are acceptable. In embodiments, a first coupling half is attached to the distal surface of the body side member at a location radially closer to the stoma-receiving opening than where one or more openings are located.

In embodiments, the first coupling half is configured as an annular ring including an upstanding flange extending axially away from the distal surface of body side member. In one embodiment, the upstanding flange is configured to be perpendicular to the distal surface of the body side member.

In embodiments, a first radial extent dimension is smaller than an internal diameter of the annular ring forming the first half of the coupling interface on the body side member. The annular ring of the first half of the coupling interface is configured to couple with a second half of the coupling interface provided on a stomal output collecting bag.

In embodiments, the stomal output collecting bag includes a front wall forming a distal side and a rear wall forming a proximal side. Each wall can be made of gas- and liquid impermeable foil-material (for example of polyethylene (PE), polyvinyl-chloride (PVC) or ethylene-vinyl-acetate (EVA)) that is welded around the edges or the rim, to form a bag defining a waste collection chamber. The bag may be welded only partly around the rim so that a discharge opening for emptying the bag is provided at the bottom of the bag. In that case, the bag may be provided with means for closing that opening. An inlet opening is provided in the rear wall and placed in the upper part of the collecting bag, so that when a user stands up, the inlet opening will locate above a midline of the collecting bag. This provides a major collecting volume portion below the inlet opening of the bag. Thus, a top of the collecting bag is defined as the portion of the bag nearest to the inlet opening, and the bottom is defined as an opposite portion of the bag.

In embodiments, only a minor surface portion of the releasable material is exposed at each of the one or more openings. Thus, only a relatively small amount of releasable material is not initially covered by the cover layer. This is advantageous in that it allows for controlling where and how quickly moisture and exudates from the stomal output can "attack" the releasable material. In other words, the structure of the cover layer can help direct the exposure of the releasable material to stomal output to only certain controlled locations. These embodiments are further advantageous in that the releasable material will not be immediately visible to the user, thereby in some implementations providing a visually simpler impression of the ostomy appliance. In embodiments, a major portion of the releasable material is at least initially generally protected by the cover layer, thereby allowing for the distal surface of the body side member, formed by the cover layer, can be gently cleaned (wiping off stomal output and already eroded/used releasable material) during an exchange of the stomal output collecting bag without inadvertently also removing still viable releasable material.

In embodiments, the releasable material comprises an adhesive. In other embodiments, the releasable material comprises a powder. In other embodiments, the releasable material comprises a liquid. In other embodiments, the releasable material comprises a gel. In other embodiments, the releasable material comprises a paste or pasta. In other embodiments, the releasable material comprises a plurality of dissolvable pellets. In yet other embodiments, the releasable material comprises a combination of any one or more of an adhesive, a powder, a liquid, a gel, a paste and/or a plurality of pellets. In embodiments, the releasable material may be provided from manufacture in one of the forms mentioned here and be configured to transition into one or more of the other forms. As one example, a paste that may start to gel and/or become a gel in response to uptake of moisture. These options each provides one or more different advantages including, but not limited to, manipulability, shelf life, suitability for different kinds of stomal output (colostomy output tends to be more solid than ileo- and urostomy output), processing characteristics and others. By selectively applying these options, individually or in combination, to meet particular requirements of a target ostomy type, the suitability of the appliance and the improvement in sealing effect reducing or eliminating the risk of leakage, can be significantly enhanced.

Particularly, in embodiments wherein the releasable material comprises an adhesive, suitable materials include adhesives, such as, but not limited to, adhesive pastes. Suitable materials for a paste-type adhesive comprise adhesives of the types disclosed in WO2010/069334. Other types of adhesive pastes are also acceptable.

In another aspect of the disclosure, use of the body side member 20 for an ostomy appliance as disclosed herein for reducing the frequency of stomal output leakage incidents in further contemplated. The advantageous effects provided by the embodiments of the body side member 20, aid in alleviating the nuisances of output leakages often encountered by users of ostomy appliances. This is at least partly achieved by the externalization of the manipulable material providing a better security against disintegration of the skin adhesive on the proximal surface of the backing film of the body side member. At the very least, use of the body side member according to the present disclosure allows for an increased wear time of an ostomy appliance.

The Neutralizing Substance

By neutralizing substance is herein meant a substance capable of neutralizing or at least minimizing the level of skin- or adhesive-aggressiveness of the output. In embodiments, the neutralizer comprises a clay, such as organophilic clay, for example bentonite or synthetic clay such as laponite. In embodiments, the neutralizing substance may be potato-derived inhibitors or protease inhibitors. Examples of potato-derived inhibitors such as potato protein is disclosed in EP 1 736 136.

In embodiments, the releasable material is in the form of a matrix composition with a neutralizing substance incorporated. The neutralizing substance may be dissolved in the matrix composition or it may be dispersed as particles in the matrix. In embodiments, the matrix may be in the form of coated neutralizing substance particles.

In embodiments, the matrix is designed to release neutralizing substance to the environment when the matrix is exposed to certain conditions. Such conditions may for example be in the presence of output from the stoma or in the presence of moisture as such.

In embodiments, the matrix is in the form of a gel, foam, film layer or paper or a coating.

In embodiments, a suitable example of a matrix composition could be an adhesive comprising 50% w/w polyisobutylene (PIB) and 25% w/w CMC and 25% w/w pectin.

In embodiments, a matrix composition in the form of a water-soluble film could be a PVOH based thermoplastic film, such as a Monosol® 7031 film from kurakay WS Film Division™, Portage, Indiana, United States.

In embodiments, the matrix is soluble in water or a component of the output. It may be slowly soluble, by slowly is herein meant that the matrix layer will not be washed away instantly, but will slowly dissolve during wear time of the wafer.

In embodiments, the matrix can absorb moisture and turn into a gel like material when wetted. The gel may be delivered in dry form but swell into a gel when brought into contact with moisture. The gel may be slowly soluble in water or in a component of the output or it may be insoluble but able to release the neutralizing substance when exposed to the output or moisture.

In embodiments, the matrix comprises polysaccharides and/or hydrocolloids. The polysaccharides or hydrocolloids may dissolve or hydrate when exposed to output, thereby releasing neutralizing substance.

In embodiments, the matrix comprises protein. In embodiments, the matrix comprises gelatine.

In embodiments, the matrix is a material capable of forming a gel when wetted. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine. In embodiments, the matrix is substantially non-adhesive. By non-adhesive is meant that it is not adhesive, though it may under certain circumstances become slightly sticky.

In another aspect, the disclosure relates to an ostomy appliance including a body side member as described herein and a stomal output collecting bag configured to be attached to the distal surface of the body side member.

In one embodiment, the ostomy appliance is a one-piece ostomy appliance, i.e. without a coupling interface between the body side member and the stomal output collecting bag. In another embodiment, the ostomy appliance is a two-piece appliance including a coupling interface for connecting a stomal output collecting bag to the body side member by connecting or coupling first and second coupling halves to each other.

In one embodiment, the stomal output collecting bag comprises a second half of a coupling interface that is configured to couple with a first half of the coupling interface on the body side member to attach the stomal collecting bag to the body side member.

In one embodiment, at least the distal surface of the body side member formed by the cover layer is defined by a first zone and a second zone surrounding the first zone, the first zone being radially inside of an annular connection between a first half of a coupling interface and the body side member, and the second zone being radially outside of the annular connection between the first half of the coupling interface and the body side member.

In one embodiment, each of the one or more openings are in the second zone of the cover layer.

DETAILED DESCRIPTION OF THE DRAWINGS

FIG. 1 is a cross-sectional view of one embodiment of a body side member 20 of an ostomy appliance according to the present disclosure. The body side member 20 includes a distal surface 22 ("overside" in FIG. 1) and a proximal surface 24 ("underside" in FIG. 1). At least a portion of the proximal surface 24 of the body side member 20 comprises an adhesive 31. At least a portion of the distal surface 22 is formed by a cover layer 36. FIG. 1 shows a stoma O of the user extending through a stoma receiving opening 32 of the body side member 20. The stoma receiving opening 32 may be provided during manufacture of the body side member 20, or it may be provided by the user in preparing the body side member 20 for attachment to the skin surface around the stoma O. The body side member 20 includes a cover layer 36 comprising one or more openings 34. A releasable material 33 is provided proximal to the cover layer 36. FIG. 1 illustrates a situation immediately after the body side member 20 has been attached to the skin surface S around the stoma O of a user.

Figure 2:
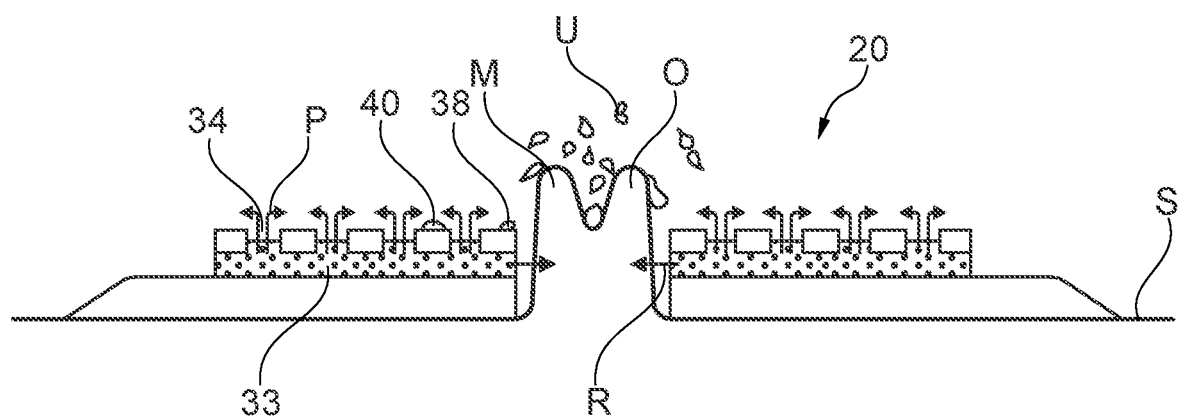
FIG. 2 is a schematic cross-sectional view of one embodiment showing a body side member comprising a releasable material.

Each of the one or more openings 34 are configured to allow egression of a releasable material 33. Thus, each opening 34 is suitable for letting a mass or volume of the releasable material 33 "escape" or exit through the one or more openings 34. This is illustrated in FIG. 2, which shows (by plurality of arrows P) how the releasable material egress through openings 34 and is released onto the distal surface 22 of the body side member 20. The releasable material 33 can thereby be shifted between at least a first position and a second position in relation to an opening 34. The releasable material 33 is shiftable between the first and the second position at least in use of the body side member 20.

FIG. 2, which is a cross-sectional view of one embodiment of the body side member 20 further illustrates how some of the releasable material 33 has begun to engage with stomal output U, illustrated by way of example at position 38. In addition to engaging with the stomal output U, the releasable material also engages with moisture (or mucin) emanating from the mucous membrane M of the stoma O, and in some situations also with moisture (sweat) emerging from the skin surface S of the user. By applying finger pressure to the distal surface 22 at or adjacent each of the openings 34, releasable material 33 egress out of the openings. Depending inter alia on the volume of stomal output U and/or moisture, a mass of releasable material 33 can egress out through the opening 34 and act as a material being "sacrificed" to the aggressive stomal output U. In some implementations, the releasable material 33 comprises one or more neutralizing substances which release or engage with the stomal output U, and thereby neutralizes the damaging contents of the stomal output such that the aggressive elements thereof do not break down the adhesive 31 of the proximal surface 24 of the body side member 20. In the embodiments shown in FIGS. 1 and 2, releasable material 33 can additionally engage with the stoma's surface at the side thereof, indicated by arrows R, and thereby help to improve the seal between the body side member 20 and the skin surface S, and/or slow or eliminate the possibility of the stomal output U of reaching the adhesive 31. However, the body side member 20 is not necessarily required to abut or be very close to the stoma's surface, as shown in FIGS. 1 and 2. In any event, the major portion of the releasable material 33 coming into engagement with the stomal output U egress out through the openings 34. Releasable material 33 having egressed out of the openings 34 can configure, e.g. by taking up moisture and/or blending with the stomal output, to collect (or gather) on the distal surface 22 of the body side member 20, i.e. in the one or more openings 34 and on the portions of the cover layer 36 not forming the openings 34, as shown at position 40 in FIG. 2. This may additionally help protect the releasable material 34 from breaking down rapidly and further to help provide a prolonged availability of releasable material 34 for use as a sacrificial material.

Figure 3:
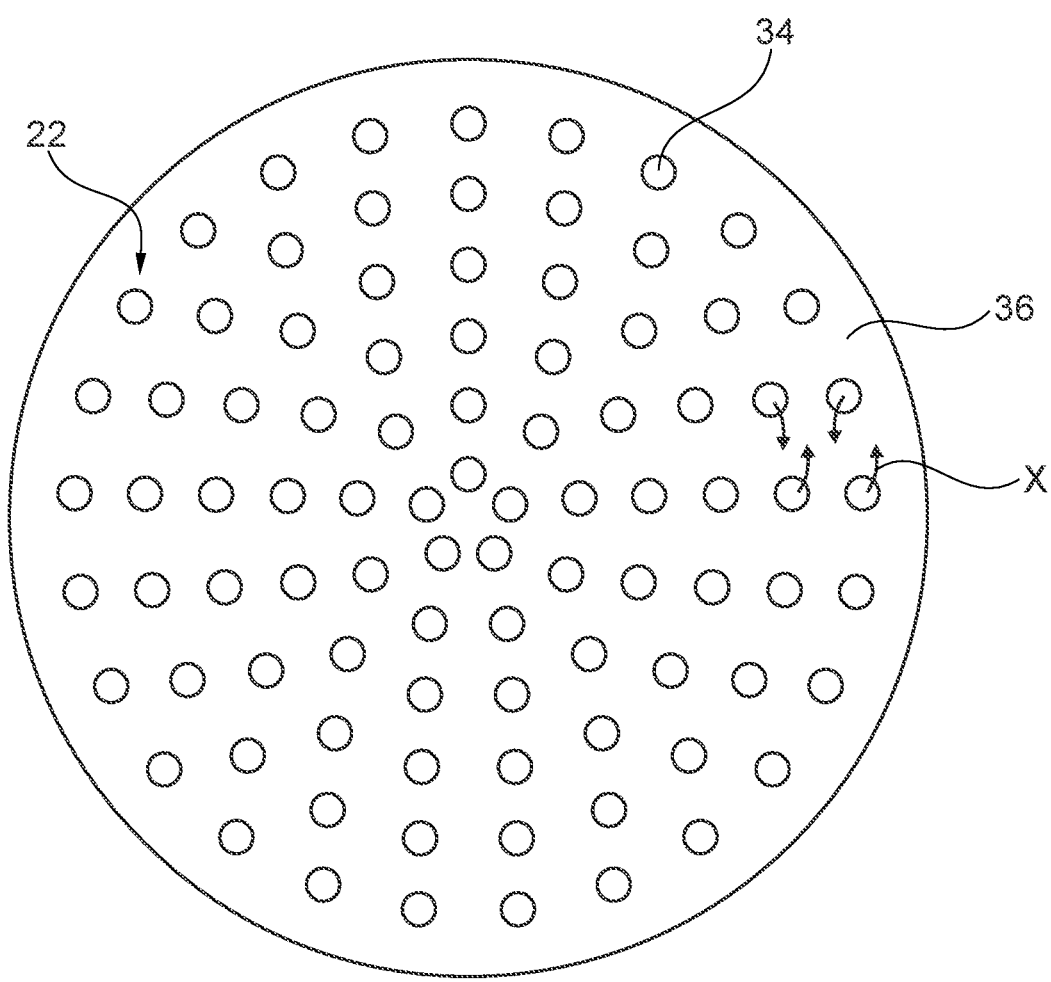
FIG. 3 is a schematic top view of one embodiment illustrating one embodiment of a cover layer of a body side member.

FIG. 3 is a schematic top view illustrating one embodiment of a cover layer 36 of the body side member 20 The cover layer 36 comprises a plurality of openings 34. As indicated by arrows X in FIG. 3, releasable material 33 can egress out of the openings 34, such as by finger pressure from a user.

By applying finger pressure on a distal surface 22 formed by the cover layer 36, releasable material 33 egresses through, or exits the openings 34 in the cover layer. Accordingly, the releasable material 33 can thus be shifted between at least a first and a second position. In the first position, the releasable material 33 is provided proximal to the cover layer 36 (underneath or below cover layer 36 in FIG. 3), and in the second position at least some of the releasable material 33 is egressed through the openings 34 onto the distal surface 22 of the body side member 20.

In the FIG. 3 embodiment, the releasable material 33 can egress or be dispensed in a distal direction, i.e. away from the skin surface of a user when the body side member 20 is in use. This allows the dispensed releasable material to "spread" over a larger area of the distal surface 22 of the body side member 20.

Figure 4:
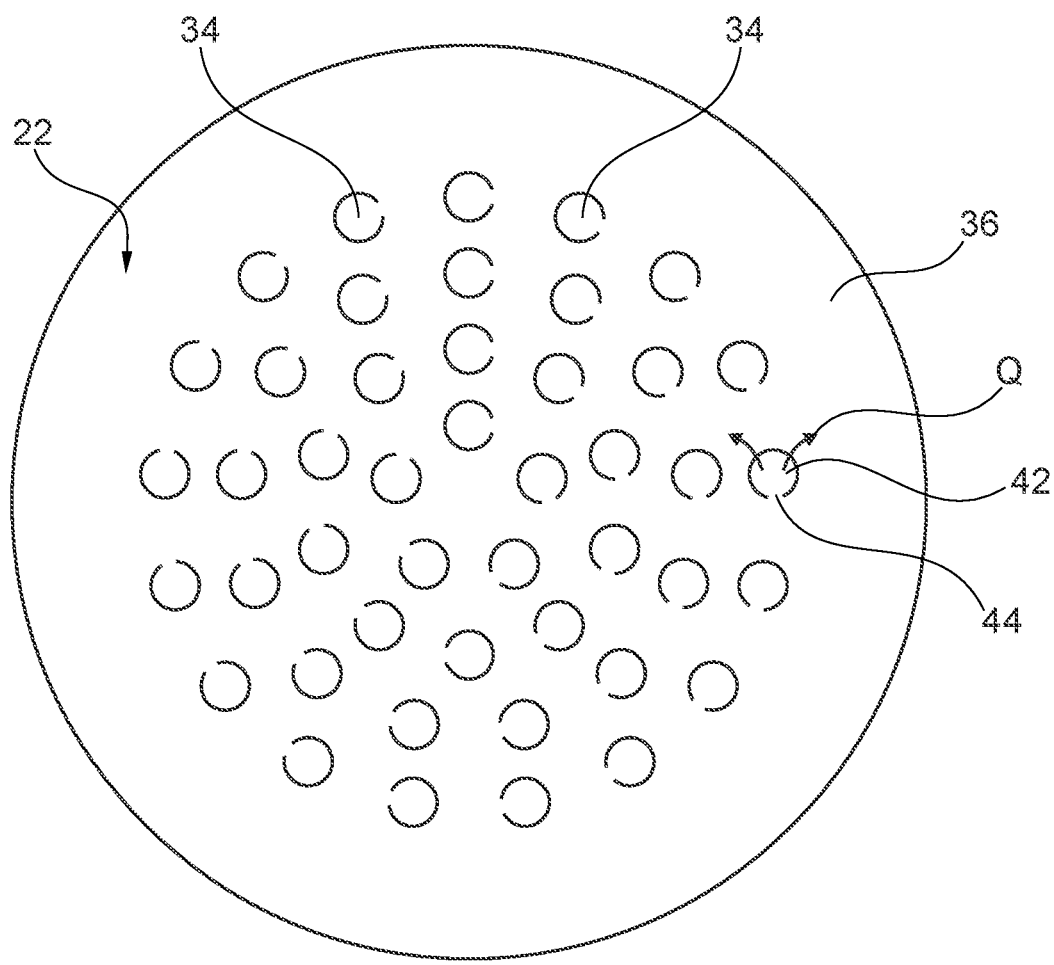
FIG. 4 is a schematic top view of one embodiment illustrating one embodiment of a cover layer of a body side member.

FIG. 4 is a schematic top view illustrating one embodiment of a cover layer 36 of the body side member 20 The cover layer 36 comprises a plurality of openings 34. Each of the openings 34 of FIG. 4 comprises a hinged gate 42 formed in the cover layer. In FIG. 4, the openings 34 are illustrated as being substantially circular, however other shapes are also possible. A hinge 44 is formed at an arc portion of the periphery of the opening 34. The hinge 44 shown in FIG. 4 provides one option for allowing the gate 42 to open to let releasable material 33 egress through the opening 34 onto the distal surface 22 of the body side member 20, as indicated by dotted arrows Q. By applying finger pressure on the distal surface 22, releasable material 33 egresses through the openings 34 in the cover layer 36. Accordingly, the releasable material 33 can be shifted between at least a first and a second position. In the first position, the releasable material 33 is provided proximal to the cover layer 36 (underneath or below cover layer 36 in FIG. 4), and in the second position at least some of the releasable material 33 is egressed through the openings 34 onto the distal surface 22 of the body side member 20. As the hinged gate 42 of the embodiment of FIG. 4 can both "open" to allow egression of releasable material 33, and "close", when releasable material is not egressing out of a respective opening 34, the hinged gate 42 can further assist in protecting the releasable material 33 from being subjected to stomal output collecting on the distal surface 22 of the body side member 20.

Figure 5:
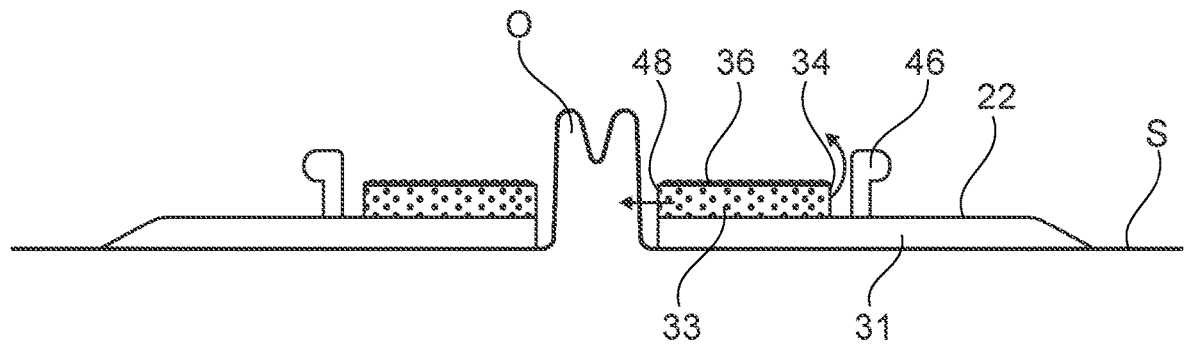

FIG. 5 is a schematic cross-sectional view of one embodiment of a cover layer 36 of a body side member 20 formed with an opening 34, which is located radially closer to a coupling ring 46 forming a first half of a coupling interface of the body side member 20, than to an innermost edge portion 48 of the body side member 20. In the embodiment of FIG. 5, it is to be understood that the opening 34 is provided annularly, or at least in a plurality of arc segments along the coupling ring 46. When finger pressure is exercised on the distal surface 22 of the cover layer 36 radially within the coupling ring 46, releasable material 33 exits from the opening 34 and onto the distal surface 22. Releasable material 33 can also be directed or guided from towards the stoma O at the innermost edge portion 48. This configuration of the opening 34 can help the user to distribute the releasable material 33 over an entirety of the distal surface 22 radially inside of the coupling ring 46.

Figure 6:
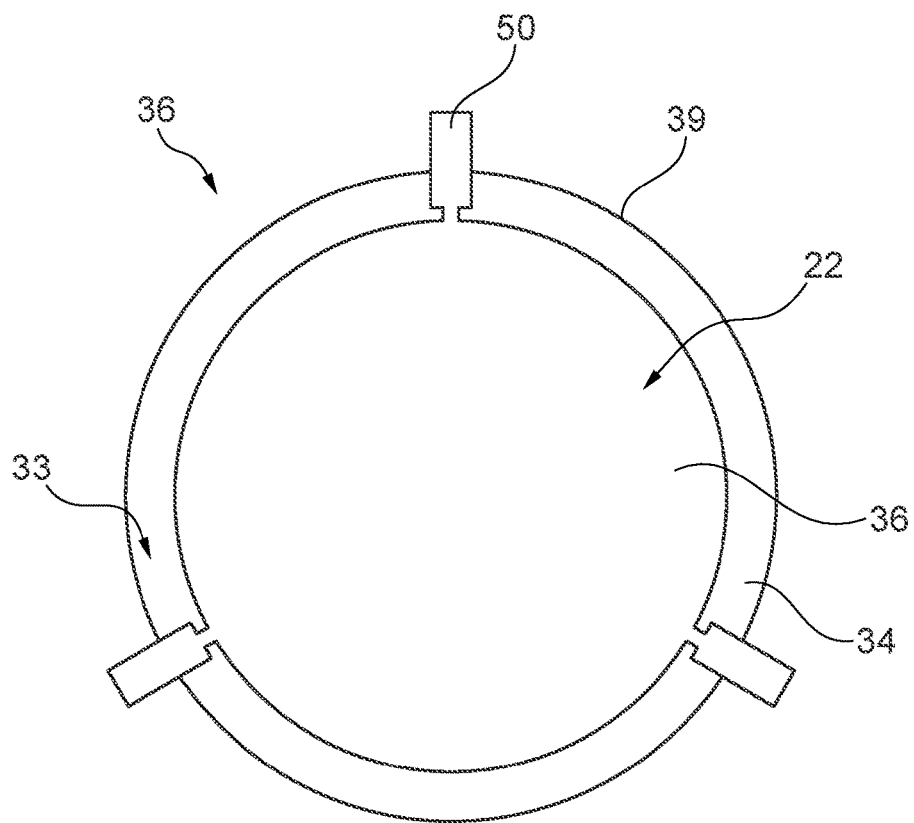
FIG. 6 is a schematic top view of one embodiment illustrating one embodiment of a cover layer of a body side member.

FIG. 6 is a schematic top view of one embodiment of a cover layer 36 wherein an opening 34 is a single annular opening 34. Releasable material 33 is dispensable through the single annular opening 34, which in the embodiment of FIG. 6 is located at a radially outermost edge portion 39 of the body side member 20. In the embodiment of the cover layer 36 illustrated in FIG. 6, the cover layer 36 further comprises three radial protrusions 50 extending from the outermost edge portion 39. The radial protrusions 50 are suitable for attaching the cover layer 36 to one or more of the other components of the body side member 20. Releasable material 33 can egress from a first position proximal to the cover layer 36 through the single annular opening 34 to a second position on the distal surface 22 of the body side member 20.

Figure 7:
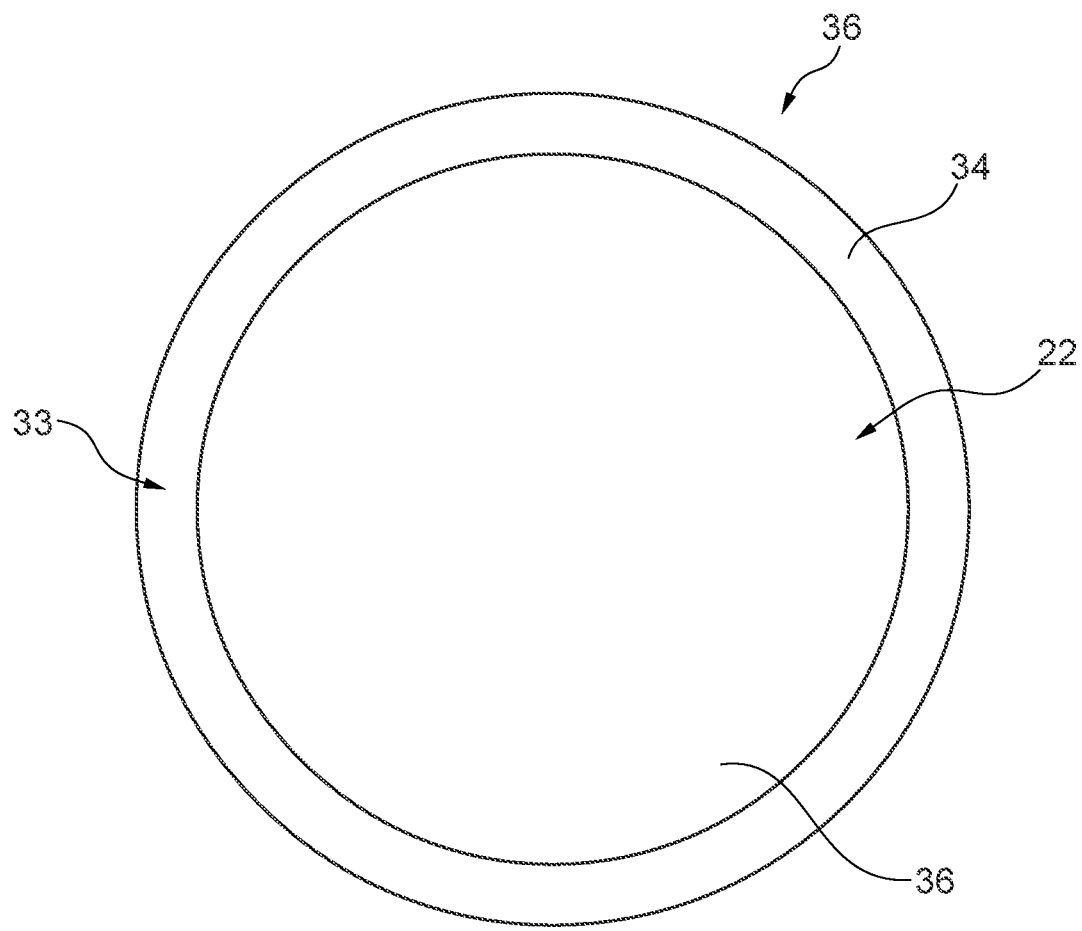
FIG. 7 is a schematic top view of one embodiment illustrating one embodiment of a cover layer of a body side member.

FIG. 7 is a schematic top view illustrating one embodiment comprising a single annular opening 34 located at a radially outermost edge portion 39 of the body side member 20. In the embodiment illustrated in FIG. 7, the cover layer 36 is a "loose" cover layer, in the sense that is does not comprise means for attaching it to the other components of the body side member 20. However, some degree of attachment of the cover layer 36 is provided by the releasable material 33. In some implementations, the releasable material 33 is adhesive, and thus capable of attaching with the cover layer 36 by adhesion. Other attachment options are possible.

Figure 8:
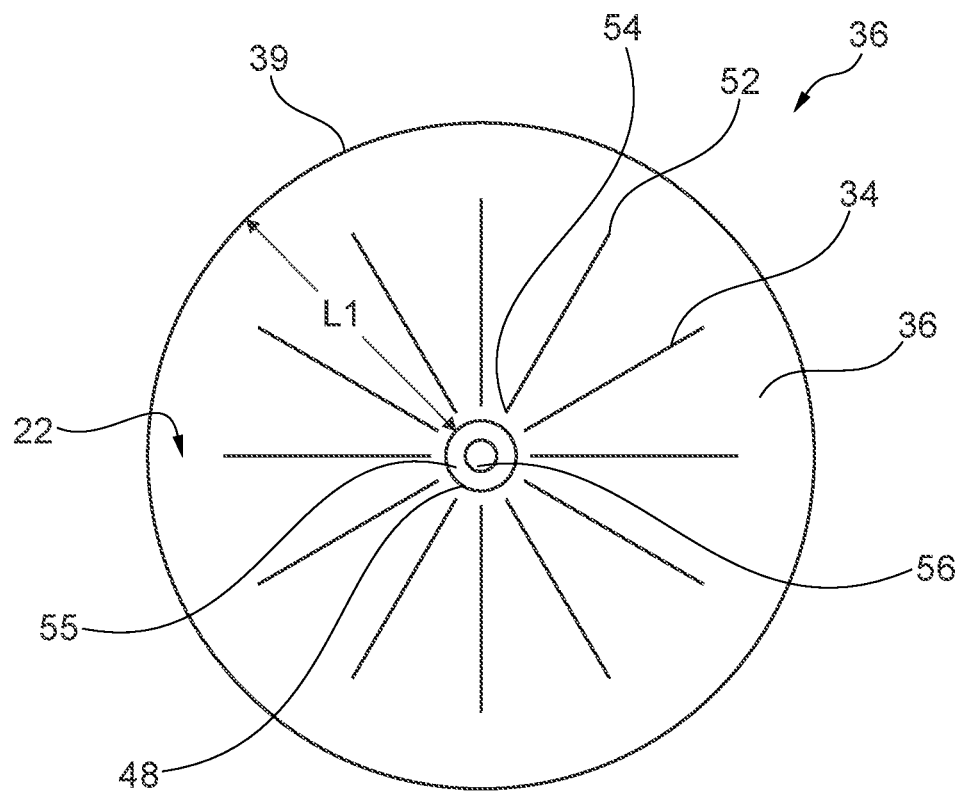
FIG. 8 is a schematic top view of one embodiment illustrating one embodiment of a cover layer of a body side member.

FIG. 8 is a schematic top view of one embodiment of a cover layer 36 of a body side member 20, wherein one or more openings 34 are provided as a plurality of slitted perforations in the cover layer 36 forming the distal surface 22 of the body side member 20. In the embodiment shown in FIG. 8, each of the slitted perforations 34 is linear. Furthermore, each of the slitted perforations 34 is provided in a straight line extending between two points 52, 54 in the radial direction of the cover layer 36. In embodiments, the straight line of each slitted perforation 34 extends from a point 54 located radially outward of a centre portion 55 of the body side member 20 to a point 52 located approximately ⅕-¼ of a radial distance LI between an innermost edge portion 48 of the body side member 20 around the stoma receiving opening 56, and an outermost edge portion 39 of the body side member 20.

Figure 9:
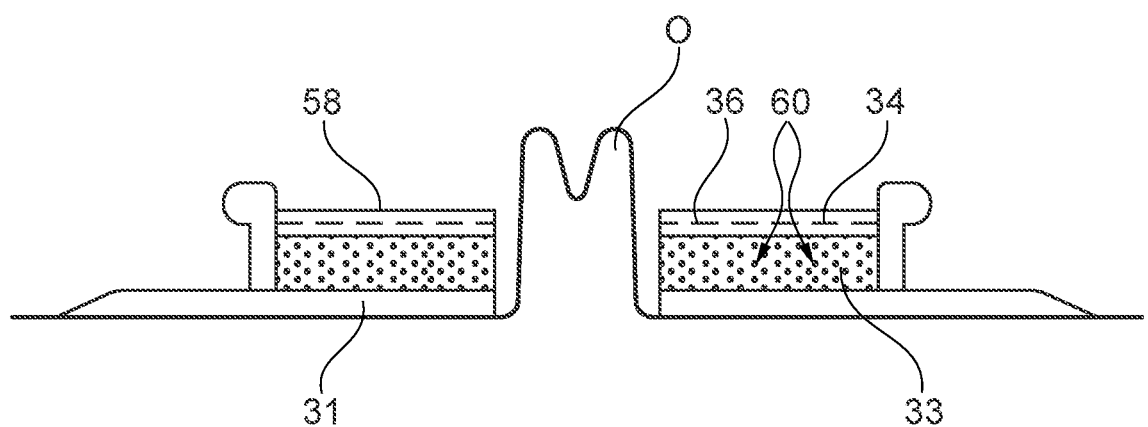
FIG. 9 is a schematic, cross-sectional view of one embodiment of a cover layer of a body side member.

FIG. 9 is a schematic cross-sectional view illustrating an embodiments wherein releasable material 33 is located proximal to a cover layer 36 formed of an erodible material. The cover layer 36 comprises openings 34. In the embodiment of FIG. 9, a relatively thin protective layer or coating 58 is provided on the distal surface of the erodible cover layer 36 to prevent or slow erosion or break-down of the releasable material 33 by aggressive stomal output gathering on the distal surface 22 of the body side member 20. The protective layer or coating 58 includes a "one-way" (unidirectionally permeable) material allowing moisture 60 to penetrate through the protective layer or coating 58 into the erodible cover layer 36, but does not allow releasable material 33 to penetrate or escape the opposite way. When a certain predeterminable amount of moisture 60 has penetrated the protective layer 58, the cover layer 36 erodes entirely away, thereby dislodging an entirety of the cover layer 36, and taking the protective layer 58 with it, i.e. causing the protective layer 58 to disappear as it is no longer attached to any other component of the body side member 20. This provides for letting an entirety of the surface area of the releasable material 33 by exposed to stomal output. Thereby, release of a majority of the releasable material can be delayed or postponed, and/or brought to occur suddenly and/or massively, e.g. if a major and potentially leakage incurring event arises.

Figure 10:
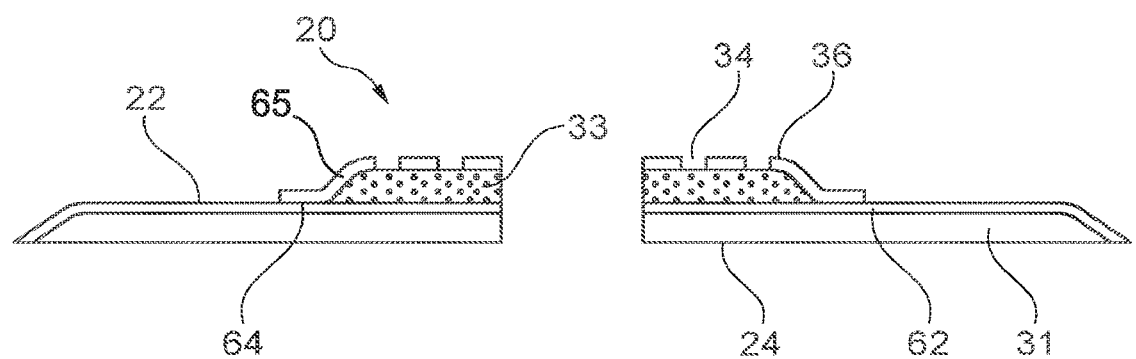
FIG. 10 is a schematic cross-sectional view of one embodiment of a body side member comprising a cover layer comprising one or more openings.

FIG. 10 is a schematic cross-sectional view of one embodiment of a body side member 20 comprising a cover layer 36 comprising one or more openings 34. A mass of releasable material 33 is located proximal to the cover layer 36. The adhesive 31 of the proximal surface 24 of the body side member 20 is provided on a backing layer. In the embodiment of FIG. 10, the releasable material 33 is provided on a distal surface of the backing layer 62 and proximal to the cover layer 36. Releasable material 33 can egress through the openings 34 and onto the distal surface 22 of the body side member 20. The releasable material 33 can thus absorb excessive stomal output before it reaches the proximal surface 24 comprising the adhesive 31 of the body side member 20. Thereby, the wear time of the body side member can be effectively extended. In the embodiment of FIG. 10, the cover layer 36 is attached to the backing layer 62 by welds, such as at location 64.

Figure 11:
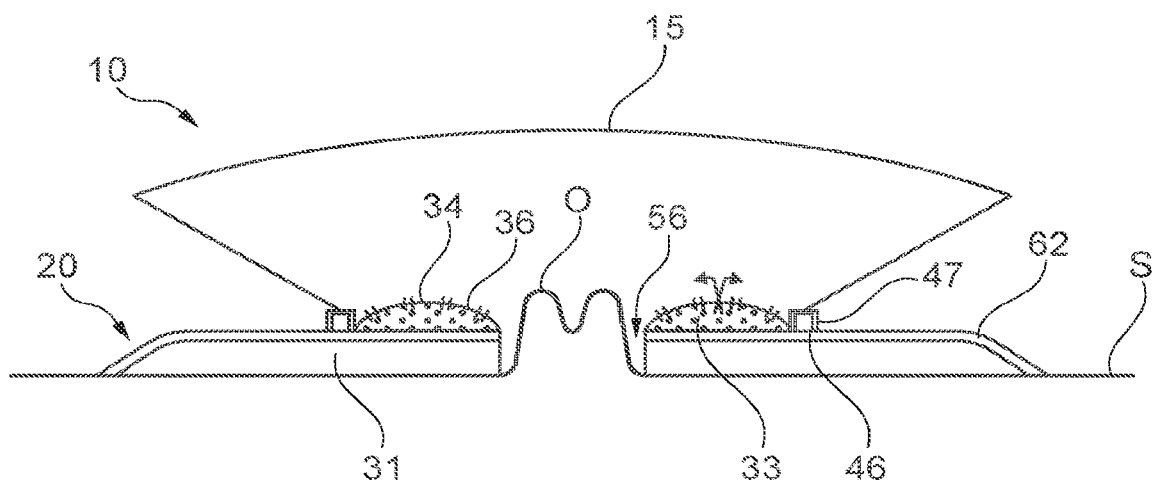
FIG. 11 is a schematic, cross-sectional view of one embodiment of an ostomy appliance comprising a body side member according to the present disclosure attached to the skin surface of a user.

FIG. 11 is a schematic cross-sectional view of one embodiment of a body side member 20 of an ostomy appliance 10 in use, i.e. attached to the skin surface S around the stoma O of a user. The body side member comprises a cover layer 36 comprising openings 34 allowing for a mass of releasable material 33 to egress onto distal surface 22. By applying finger pressure through the distal foil layer 65 of the stomal output collecting bag 15, a user can externalize and make releasable material 33 egress openings 34 onto the distal surface 22.

FIG. 11 further illustrates that the distal surface 22 of the body side member includes a first half 46 of a coupling interface for coupling the body side member 20 to a second half 47 of the coupling interface provided on the stomal output collecting bag 15.

In the embodiment of FIG. 11, the first coupling half 46 is an annular ring comprising an upstanding flange protruding from and perpendicular to the distal surface 22 of the body side member 20. The flange is configured for attaching the second coupling half 47 in the form of a coupling ring provided on the stomal output collecting bag 15. In embodiments, the first coupling half 46 is attached to the distal surface 22 by an adhesive or by welding, but other ways of attaching are acceptable.

FIG. 11 illustrates one embodiment of an ostomy appliance 10 including a body side member 20 as described herein and a stomal output collecting bag 15 configured to attached to the distal surface 22 of the body side member 20. In FIG. 11, the distal surface 22 of the body side member 20 comprises a plurality of openings 34. As illustrated in FIG. 11, the ostomy appliance 10 is a two-piece appliance including a coupling interface comprising a first half 46 and a second half 47 for connecting a stomal output collecting bag 15 to the body side member 20. It is to be understood that the ostomy appliance 10 may also be a one-piece ostomy appliance, i.e. without a coupling interface between the body side member 20 and the stomal output collecting bag 15.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A body side member of an ostomy appliance, the body side member comprising:
   an adhesive that forms at least a portion of a proximal surface of the body side member, where the adhesive is adapted to secure the body side member to skin;
   a cover layer that forms a distal surface of the body side member;
   a releasable material between the adhesive and the cover layer, where the releasable material includes a neutralizer;
   a stoma receiving opening extending through the adhesive and the cover layer of the body side member, where the stoma receiving opening is adaptable for placement over a stoma; and
   a plurality of openings formed in and extending through the cover layer;
   wherein the releasable material is configured to swell in response to absorption of moisture from a stomal output and the neutralizer is released from the releasable material and passes through the plurality of openings formed through the cover layer to neutralize enzymes in the stomal output present on the distal surface of the body side member.

2. The body side member of claim 1, wherein the cover layer comprises a sheet material attached to the releasable material.

3. The body side member of claim 1, wherein the cover layer is formed as an integral component of the body side member.

4. The body side member of claim 1, wherein the plurality of openings comprises circular perforations in the cover layer.

5. The body side member of claim 4, wherein each circular perforation has a widest diameter in a range of 2-10 mm.

6. The body side member of claim 1, wherein the plurality of openings is localized in a zone of the cover layer between the stoma receiving opening and an outermost edge of the body side member.

7. The body side member of claim 1, wherein the plurality of openings comprises a distribution of slits formed in the cover layer between the stoma receiving opening and an outermost edge of the body side member.

8. The body side member of claim 1, wherein each of the plurality of openings comprises a hinged gate formed in the cover layer.

9. The body side member of claim 1, further comprising one opening at an outermost edge of the cover layer.

10. The body side member of claim 1, wherein the neutralizer from the releasable material is passed through the plurality of openings in response to finger pressure applied to the cover layer.

11. The body side member of claim 1, wherein the releasable material provides a matrix for delivery of the neutralizer and comprises at least one of an adhesive, a powder, a paste, a liquid, a gel, a plurality of pellets or any combination thereof contained within the matrix.

12. The body side member of claim 1, wherein the releasable material is viscoelastic.

13. The body side member of claim 1, wherein the cover layer comprises a thermoformable material.

14. The body side member of claim 1, wherein the cover layer comprises a dissolvable material adapted to dissolve in response to the stomal output.

15. The body side member of claim 1, further comprising a backing layer, with the adhesive applied to a proximal side of the backing layer; wherein the releasable material is provided in a layer deposited on a distal side of the backing layer.

16. The body side member of claim 1, further comprising:
   an ostomy bag attachable to the body side member;
   wherein the ostomy bag is provided to collect the stomal output from the stoma and the neutralizer from the releasable material is adapted to move into the ostomy bag.

17. The body side member of claim 9, wherein a diameter of the cover layer is less than a diameter of the body side member such that the one opening at the outermost edge of the cover layer is an annular opening.

18. The body side member of claim 1, wherein the neutralizer comprises a protease inhibitor.

19. The body side member of claim 1, wherein the releasable material is a moldable paste.

20. The body side member of claim 1, wherein the releasable material is an adhesive paste.

21. The body side member of claim 1, wherein the releasable material is in contact with the adhesive.

22. An ostomy appliance comprising:
   an ostomy bag attachable to a distal surface of a body side member, with the body side member comprising:
      an adhesive applied to a proximal surface of the body side member, where the adhesive is adapted to secure the body side member to skin;
      a cover layer that forms a distal surface of the body side member;
      a releasable material between the adhesive and the cover layer, where the releasable material includes a neutralizer;
      a stoma receiving opening extending through the body side member, where the stoma receiving opening is adaptable for placement over a stoma; and
      a spiral opening formed in the cover layer;
      wherein the releasable material is configured to swell in response to absorption of moisture from a stomal output and the neutralizer is released from the releasable material and passes through the spiral opening formed in the cover layer to neutralize enzymes in the stomal output present within the ostomy bag on the distal surface of the body side member.

23. The ostomy appliance of claim 22, wherein the neutralizer is adapted to be squeezed from the releasable material through the spiral opening by a user.

24. The body side member of claim 1, wherein the neutralizer is released upon swelling of the releasable material.

25. The body side member of claim 1, wherein the releasable material egresses through a portion of the plurality of openings upon swelling.

* * * * *